(12) United States Patent
Sniffin et al.

(10) Patent No.: US 9,907,550 B2
(45) Date of Patent: Mar. 6, 2018

(54) STITCHING DEVICE WITH LONG NEEDLE DELIVERY

(71) Applicant: Covidien LP, Mansfield, MA (US)

(72) Inventors: Kevin Sniffin, Danbury, CT (US);
Mark Russo, Plantsville, CT (US);
Gregory Fischvogt, Hamden, CT (US);
Russell Pribanic, Roxbury, CT (US);
Eric Taylor, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 620 days.

(21) Appl. No.: 14/556,780

(22) Filed: Dec. 1, 2014

(65) Prior Publication Data

US 2015/0209028 A1    Jul. 30, 2015

Related U.S. Application Data

(60) Provisional application No. 61/931,713, filed on Jan. 27, 2014.

(51) Int. Cl.
*A61B 17/04*  (2006.01)
*A61B 17/062*  (2006.01)
*A61B 17/06*  (2006.01)

(52) U.S. Cl.
CPC ...... *A61B 17/0469* (2013.01); *A61B 17/0625* (2013.01); *A61B 17/0482* (2013.01); *A61B 2017/06047* (2013.01)

(58) Field of Classification Search
CPC ............ A61B 17/0469; A61B 17/0482; A61B 17/0625; A61B 2017/2926
See application file for complete search history.

(56) References Cited

U.S. PATENT DOCUMENTS

| | | | |
|---|---|---|---|
| 1,037,864 A | 9/1912 | Carlson et al. |
| 1,131,163 A | 3/1915 | Saunders et al. |
| 1,293,565 A | 2/1919 | Smit |
| 1,449,087 A | 3/1923 | Bugbee |
| 1,876,792 A | 9/1932 | Thompson |
| 2,213,830 A | 9/1940 | Anastasi |
| 2,880,728 A | 4/1959 | Rights |
| 3,090,386 A | 5/1963 | Curtis |
| 3,349,772 A | 10/1967 | Rygg |
| 3,470,875 A | 10/1969 | Johnson |
| 3,807,407 A | 4/1974 | Schweizer |
| 3,842,840 A | 10/1974 | Schweizer |
| 3,901,244 A | 8/1975 | Schweizer |
| 3,946,740 A | 3/1976 | Bassett |
| 4,021,896 A | 5/1977 | Stierlein |
| 4,109,658 A | 8/1978 | Hughes |
| 4,161,951 A | 7/1979 | Scanlan, Jr. |
| 4,164,225 A | 8/1979 | Johnson et al. |
| 4,236,470 A | 12/1980 | Stenson |

(Continued)

*Primary Examiner* — Sarah W Aleman

(57) ABSTRACT

An end effector assembly for a surgical stitching device is provided. The end effector assembly includes an end effector, a housing, and a needle. The end effector includes a first jaw member and a second jaw member. The housing is movable relative to the end effector. The needle is releasably coupled to the housing and movable relative to the housing between a first, insertion position and a second deployed position. The needle is adapted, when in the second, deployed position, to releasably couple to one or both of the first jaw member and the second jaw member of the end effector.

15 Claims, 3 Drawing Sheets

(56) References Cited

U.S. PATENT DOCUMENTS

| | | |
|---|---|---|
| 4,345,601 A | 8/1982 | Fukuda |
| 4,373,530 A | 2/1983 | Kilejian |
| 4,471,781 A | 9/1984 | Di Giovanni et al. |
| 4,491,135 A | 1/1985 | Klein |
| 4,580,567 A | 4/1986 | Schweitzer et al. |
| 4,621,640 A | 11/1986 | Mulhollan et al. |
| 4,635,638 A | 1/1987 | Weintraub et al. |
| 4,890,615 A | 1/1990 | Caspari et al. |
| 4,923,461 A | 5/1990 | Caspari et al. |
| 4,935,027 A | 6/1990 | Yoon |
| 4,957,498 A | 9/1990 | Caspari et al. |
| 5,059,201 A | 10/1991 | Asnis |
| 5,100,421 A | 3/1992 | Christoudias |
| 5,171,257 A | 12/1992 | Ferzli |
| 5,181,919 A | 1/1993 | Bergman et al. |
| 5,207,693 A | 5/1993 | Phillips |
| 5,217,471 A | 6/1993 | Burkhart |
| 5,242,458 A | 9/1993 | Bendel et al. |
| 5,254,126 A | 10/1993 | Filipi et al. |
| 5,261,917 A | 11/1993 | Hasson et al. |
| 5,281,220 A | 1/1994 | Blake, III |
| 5,336,230 A | 8/1994 | Leichtling et al. |
| 5,454,823 A | 10/1995 | Richardson et al. |
| 5,674,229 A | 10/1997 | Tovey et al. |
| 5,980,538 A * | 11/1999 | Fuchs ................ A61B 17/0469 606/139 |
| 8,337,515 B2 | 12/2012 | Viola et al. |
| 8,628,545 B2 | 1/2014 | Cabrera et al. |

\* cited by examiner

STITCHING DEVICE WITH LONG NEEDLE DELIVERY

CROSS-REFERENCE TO RELATED APPLICATIONS

This application claims the benefit of and priority to U.S. Provisional Patent Application No. 61/931,713, filed Jan. 27, 2014, the entire disclosure of which is incorporated by reference herein.

TECHNICAL FIELD

The present disclosure relates to devices, systems, and methods for endoscopic suturing or stitching and, more particularly, to end effectors, systems, and methods for endoscopic suturing and/or stitching through an access device such as a cannula.

BACKGROUND

Increasingly, more and more surgical procedures are being performed through small openings (e.g., an incision or a natural opening) in the skin with the goal of reducing the invasiveness of the procedures. As compared to the larger openings typically required in traditional procedures, smaller openings result in less trauma to the patient. By reducing the trauma to the patient, the time required for recovery is also reduced. Generally, the surgical procedures that are performed through small openings in the skin are referred to as "endoscopic." If the procedure is performed on the patient's abdomen, the procedure is referred to as "laparoscopic." Throughout the present disclosure, the term "minimally invasive" is to be understood as encompassing both endoscopic and laparoscopic procedures. Cannulas can be utilized during a minimally invasive procedure to facilitate passage of endoscopic instruments.

In many surgical procedures, including those involved in endoscopic surgery, it is often necessary to suture bodily organs or tissue. Endoscopic suturing procedures can be challenging due to the small openings through which the suturing of bodily organs or tissues must be accomplished. Typically, the dimensions of the needles of endoscopic stitching devices are restricted by spatial limitations of the cannulas utilized to introduce the stitching devices into the surgical site.

It would be advantageous to have an end effector of an endoscopic stitching device that can be advanced through spatially limited access devices (e.g., cannulas) while supporting long needles. The advancement of stitching devices with long needles into surgical sites would enable a clinician to suture tissue with larger thickness as compared to stitching devices with short needles.

SUMMARY

End effector assemblies for a surgical stitching device described herein include a rotatable mounting member. The rotatable mounting member retains a needle in a first, insertion position generally in alignment with the longitudinal axis of end effector assembly and a second, deployed position generally transverse to the longitudinal axis of the end effector assembly.

In embodiments, the end effector assembly includes an end effector, a housing, and a needle. The end effector defines a longitudinal axis and includes a first jaw member and a second jaw member. The first jaw member is pivotable relative to the second jaw member between open and closed configurations.

The housing is movable relative to the end effector. In some embodiments, the housing is axially movable along the longitudinal axis relative to the first and second jaw members. In some embodiments, the housing is C-shaped.

The needle is releasably coupled to the housing and movable relative to the housing between a first, insertion position and a second, deployed position. The needle is adapted, when in the second, deployed position, to releasably couple to at least one of the first jaw member and the second jaw member of the end effector. In embodiments, the needle is rotatable relative to the housing.

In certain embodiments, the housing includes a mounting member adapted to releasably couple the needle to the housing and enable the needle to rotate between the first, insertion position and the second, deployed position. The mounting member can include a pair of protuberances that defines a channel between the pair of protuberances. The channel is adapted to receive the needle.

According to one aspect, a housing is operably coupled to the first and second jaw members of the end effector. The housing can be axially movable relative to the first and second jaw members of the end effector. In some embodiments, the housing includes a mounting member that is adapted to releasably secure a needle to the housing and enable the needle to rotate relative to the housing.

In embodiments, the needle is selectively supported on the housing and adapted to rotate about an axis of rotation that extends through the housing transverse to the longitudinal axis of the end effector. The needle can be rotatable between a first position and at least a second position when supported on the housing. The centerline of the needle may be longitudinally aligned with the longitudinal axis of the end effector in the first position and may be angled relative to the longitudinal axis of the end effector in the second position.

According to another aspect, a surgical stitching device is provided. The surgical stitching device includes a handle, an elongate member extending from the handle, and an end effector assembly supported on the elongate member. The end effector assembly includes an end effector, a housing, and a needle. The end effector is movable between open and closed states. The end effector defines a height measured between a bottom-most surface of the end effector and a top-most surface of the end effector.

The end effector defines a longitudinal axis and includes a first jaw member, a second jaw member, and a body member. The first and second jaw members are pivotably coupled to the body member. The body member defines a recess.

The housing is operably coupled to the first and second jaw members of the end effector. The housing includes a mounting member and is axially movable relative to the first and second jaw members of the end effector between an extended state and a retracted state. The mounting member is receivable within the recess of the body member of the end effector to releasably retain the housing in the retracted state.

In embodiments, the needle is releasably supported on the housing by the mounting member and adapted to selectively couple to at least one of the first and second jaw members.

In some embodiments, the needle defines a working length that is greater than the height of the end effector.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Minimally invasive suturing devices in accordance with the present disclosure enable the use of a needle that is longer than a width of a suturing device and/or an access device used to deliver the suturing device to the surgical site. Delivery of such a relatively long needle is achieved by mounting the needle to a housing of the suturing device in a first, insertion position and, once delivered to the surgical site, moving the needle to a second, deployed position. When in the deployed position, the needle is released from the housing and secured to one of two opposed jaw members of the suturing device. Minimally invasive suturing can then be achieved by passing the needle back and forth between the two opposed jaw members in a conventional manner.

For a more detailed description of suitable endoscopic surgical devices, systems, and methods for use with the present disclosure, reference can be made, for example, to U.S. Pat. No. 8,337,515 and to U.S. Patent Application Publication No. 2009/0312773, the entire contents of each of which are incorporated herein by reference. Details of various embodiments of minimally invasive suturing devices in accordance with the present disclosure will now be described in detail.

As used in the following detailed description, the term "clinician" refers to a doctor, nurse, or other health care provider and may include support personnel. The terms "proximal" or "trailing" each refer to a portion of a structure closer to a clinician, and the terms "distal" or "leading" each refer to a portion of a structure farther from the clinician.

Figure 1:
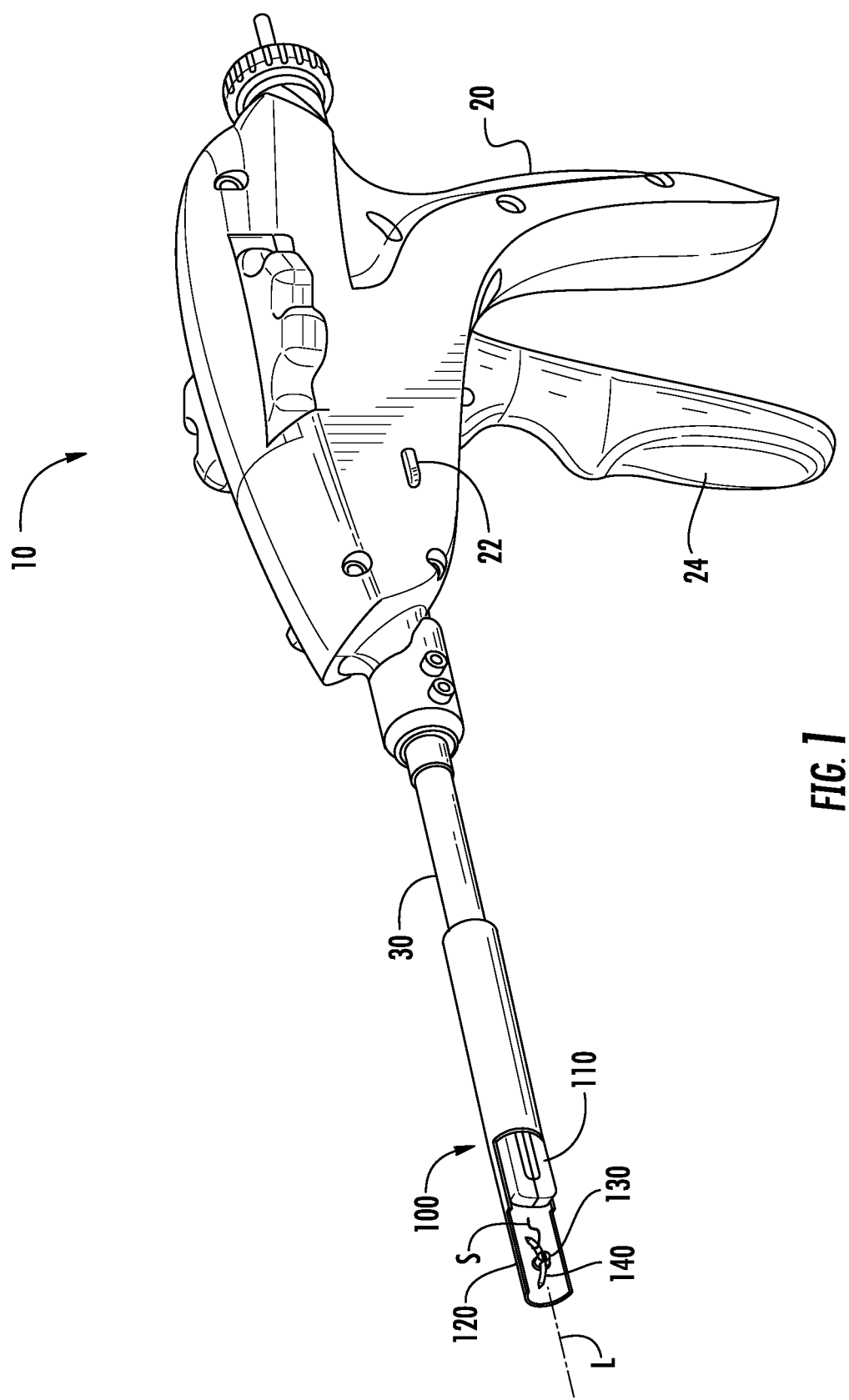
FIG. 1 is a perspective view of an embodiment of an endoscopic stitching device in accordance with the present disclosure.

Referring now in specific detail to the drawings, in which like reference numbers identify similar or identical elements, FIG. 1 illustrates an embodiment of an endoscopic stitching device, shown generally at 10. Endoscopic stitching device 10 includes a handle assembly 20 with an actuator 22 and a trigger 24 (or other suitable actuating mechanism such as a robot, etc.). An elongate tubular body portion 30 extends distally from handle assembly 20, and supports an end effector assembly 100 on the distal end portion of elongate tubular body portion 30. End effector assembly 100 can be remotely operated by handle assembly 20, for example, by actuator 22 and/or trigger 24.

End effector assembly 100 includes an end effector 110, a housing 120 slidably supported over end effector 110, a mounting member 130 rotatably mounted on housing 120, and a surgical needle 140 which is releasably coupled to mounting member 130 and is adapted to support a suture "S" to effectuate a suturing procedure. End effector assembly 100 defines a longitudinal axis "L" that extends through proximal and distal end portions of end effector assembly 100.

Figure 2:
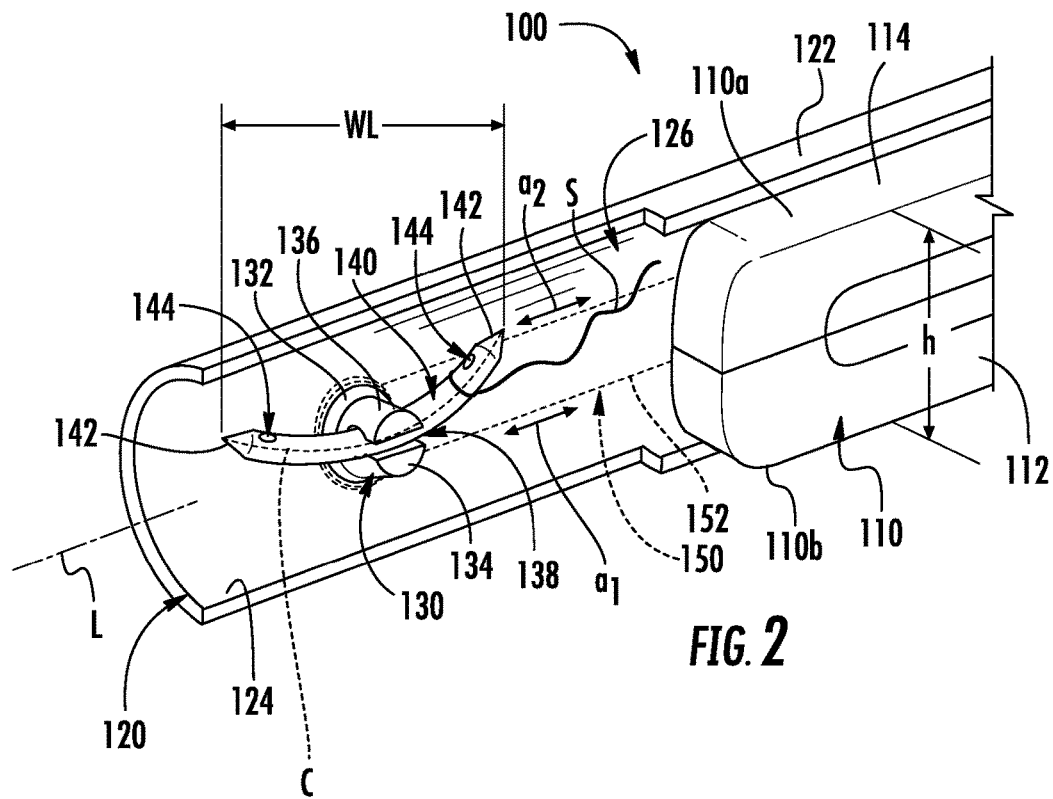
FIG. 2 is a perspective view of a distal end portion of an embodiment of an end effector assembly of the endoscopic stitching device of FIG. 1, the end effector assembly including an end effector, a housing, and a needle, the end effector shown in a closed state, the housing shown in an advanced state, and the needle shown in a first, insertion position on the housing.
Figure 3:
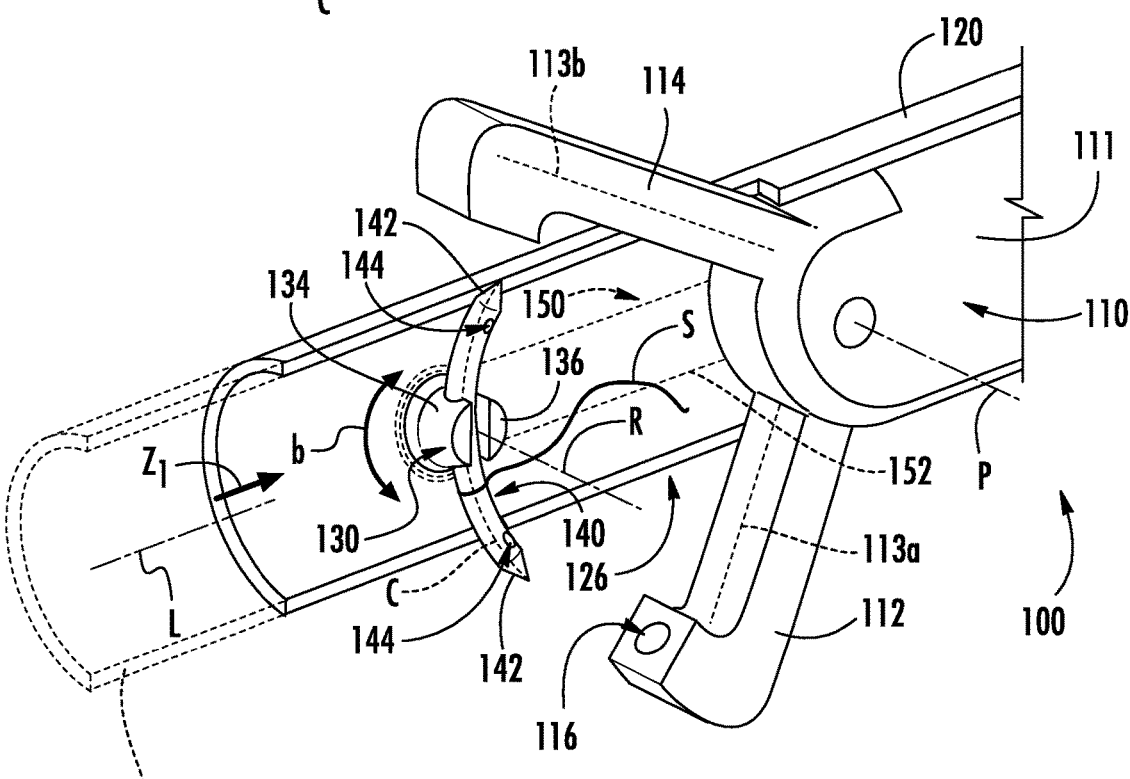
FIG. 3 is a perspective view of the distal end portion of the end effector assembly of FIG. 2 illustrating the end effector in an open state, the housing in a first retracted state, and the needle in a second, deployed position on the housing.

With reference to FIGS. 2 and 3, end effector 110 is adapted to be particularly useful in endoscopic or laparoscopic procedures wherein an endoscopic portion of the stitching device, i.e., end effector 110, is insertable into a surgical site, via an access device (e.g., trocar, cannula, etc.) (not shown) or the like. End effector 110 includes a first jaw member 112 and a second jaw member 114. One or both of first and second jaw members 112, 114 can be adapted to pivot relative to the other of first and second jaw members 112, 114. Each jaw member 112, 114 releasably supports surgical needle 140 in a needle receiving recess 116 (see FIG. 3) defined in each respective jaw member 112, 114. Surgical needle 140 is adapted to be secured to the suture "S" before insertion of end effector 110 into the surgical site or shortly after insertion of end effector 110 into the surgical site. As can be appreciated, the suture "S" can be secured to needle 140 using any conventional method. For example, the suture "S" can be secured to needle 140 by tying and/or knotting the suture "S" to a needle 140 (e.g., by looping around an outer surface of needle 140). Alternatively, and or additionally, needle 140 can define any number of apertures (not shown) into and/or through which suture "S" may be secured.

End effector 110 has a top-most surface 110a and a bottom-most surface 110b. End effector 110 is adapted to move between closed (FIG. 2) and open states (FIG. 3). In the closed state, end effector 100 defines a height "h" that is measured between top-most surface 110a and bottom-most surface 110b. As seen in FIG. 2, needle 140 defines a working length "WL" that can be any suitable dimension. In some embodiments, the working length "WL" of needle 140 is greater than the height "h" of end effector 110 in the closed state. In certain embodiments, the working length "WL" of needle 140 is equal to height "h" of end effector 110 in the closed state.

Referring to FIG. 3, end effector 100 includes a body member 111 that supports a first jaw member 112 and a second jaw member 114. First and second jaw members 112, 114 are mounted to body member 111 and extend distally from a distal end portion of body member 111. One or both of first and second jaw members 112, 114 can be adapted to pivot relative to the other of first and second jaw members 112, 114 about a pivot axis "P" between the closed state and the open state. Each of first and second jaw members 112, 114 defines a needle receiving recess 116 in a distal end portion of the respective jaw member. Each needle receiving recess 116 is adapted to receive an end portion of a pair of opposed end portions 142 of needle 140 in releasable friction fit relation.

As described in U.S. Pat. No. 8,337,515 referenced above and as shown in FIG. 3, needle 140 can define an opening 144 at each end portion 142 of needle 140. In some embodiments, needle 140 defines a single opening that extends between each end portion 142 of needle 140. Each of first and second jaw members 112, 114 can support an axially movable grasping member such as grasping members 113a, 113b. Each grasping member 113a, 113b can releasably engage one of the pair of openings 144 of needle 140 (or an end of the single opening discussed above), alternately with the other grasping member 113a, 113b, to support needle 140 in a respective one of jaw members 112, 114 to enable needle 140 to be passed back and forth between first and second jaw members 112, 114.

Referring again to FIG. 2, housing 120 extends longitudinally between proximal and distal end portions. Housing 120 includes an outer surface 122 and an inner surface 124. A passage 126 is defined at the distal end portion of housing 120 and extends through inner and outer surfaces 122, 124. Housing 120 is shown with a distal end portion thereof being formed in a C-shape, but housing 120, or portions thereof, may be formed in any suitable shape including circular and other non-circular configurations.

As seen in FIGS. 2 and 3, mounting member 130 is rotatably secured to housing 120 and extends from inner surface 124 of housing 120 in a direction transverse to longitudinal axis "L" of end effector assembly 100. Mounting member 130 includes a base 132, a first protuberance 134, and a second protuberance 136. First and second protuberances 134, 136 define a channel 138 that is dimensioned to releasably receive needle 140 so that each of the pair of opposed end portions 142 of needle 140 is exposed for selective engagement with one of jaw members 112, 114 of end effector 110.

With continued reference to FIGS. 2 and 3, mounting member 130 is rotatable relative to housing 120 about an axis of rotation "R" that extends in a direction transverse to longitudinal axis "L." As can be appreciated, mounting member 130, or portions thereof, can be configured to rotate, about axis of rotation "R," to any suitable angle, for example, between, and including, 0 and 360 degrees. In some embodiments, the angle of rotation can be limited, for example, to between, and including, 0 and 90 degrees.

Mounting member 130 can be rotated by an actuation mechanism 150 that can include a cable 152 (or multiple cables) secured to base 132 of mounting member 130. A securement of cable 152 to mounting member 130 enables mounting member 130 to rotate, as indicated by arrow "b" (FIG. 3), in response to axial translation of cable 152, as indicated by arrows "$a_1$" and "$a_2$" (FIG. 2). Actuation mechanism 150 can include any suitable actuator (e.g., knob, slide, button, etc.) such as actuator 22 (FIG. 1), which may be coupled to a handle (e.g., handle assembly 20) for remotely imparting rotational movement, upon an actuation of the actuator, to mounting member 130 and, thus, needle 140 (i.e., when needle 140 is secured to mounting member 130).

Actuation mechanism 150 can include any suitable mechanical and/or electrical component adapted to impart rotation upon mounting member 130, or portions thereof. In embodiments, actuation mechanism 150 can include any number of springs, levers, gears, cables, electrical circuitry, and the like that are adapted to cooperate to rotate mounting member 130, or portions thereof.

In use, end effector assembly 100 can be advanced to a surgical site (not shown), for example, through an access device (not shown) such as a cannula assembly.

As seen in FIG. 2, end effector assembly 100 is positionable in an insertion state, for example, to advance end effector assembly 100 through an access device or small opening. In the insertion state, housing 120 is disposed in an advanced or extended state relative to end effector 110, where a distal end portion of housing 120 is disposed forward, or distally of, end effector 110. In the insertion state of the end effector assembly 100, end effector 110 is disposed proximally of opening 126 of housing 120, and retained in the closed state by virtue of an engagement with inner surface 124 of housing 120. Mounting member 130 can be positioned so that a centerline "C" of needle 140, which is supported by mounting member 130, can be arranged in longitudinal aligned relation with longitudinal axis "L" of end effector assembly 100, e.g., the first, insertion position of needle 140. While arranged in this longitudinally aligned position, channel 138 of mounting member 130 and centerline "C" of needle 140 can be adapted to be coaxially aligned with, or spaced apart and parallel to, longitudinal axis "L" of end effector assembly 100.

With reference to FIG. 3, housing 120 can be slid proximally relative to end effector 110, as indicated by arrow "$Z_1$," to a needle grasping position, or a first retracted state. In the first retracted state, jaw members 112 and 114 of end effector 110 can be pivoted to the open state through opening 126 of housing 120, for example, upon being advanced to the surgical site. Shortly before, simultaneously therewith, or shortly thereafter, mounting member 130, and thus needle 140 (supported by mounting member 130), can be rotated, for example, upon an actuation of actuator 22, to the second, deployed position (e.g., 90 degrees offset from the longitudinally aligned position described above). In the second, deployed position, the pair of opposed end portions 142 of needle 140 can be aligned, or substantially aligned with needle receiving recesses 116 of jaw members 112, 114 of end effector 110 to couple needle 140 to one or both of jaw members 112, 114 of end effector 110 and separate needle 140 from mounting member 130.

Figure 4:
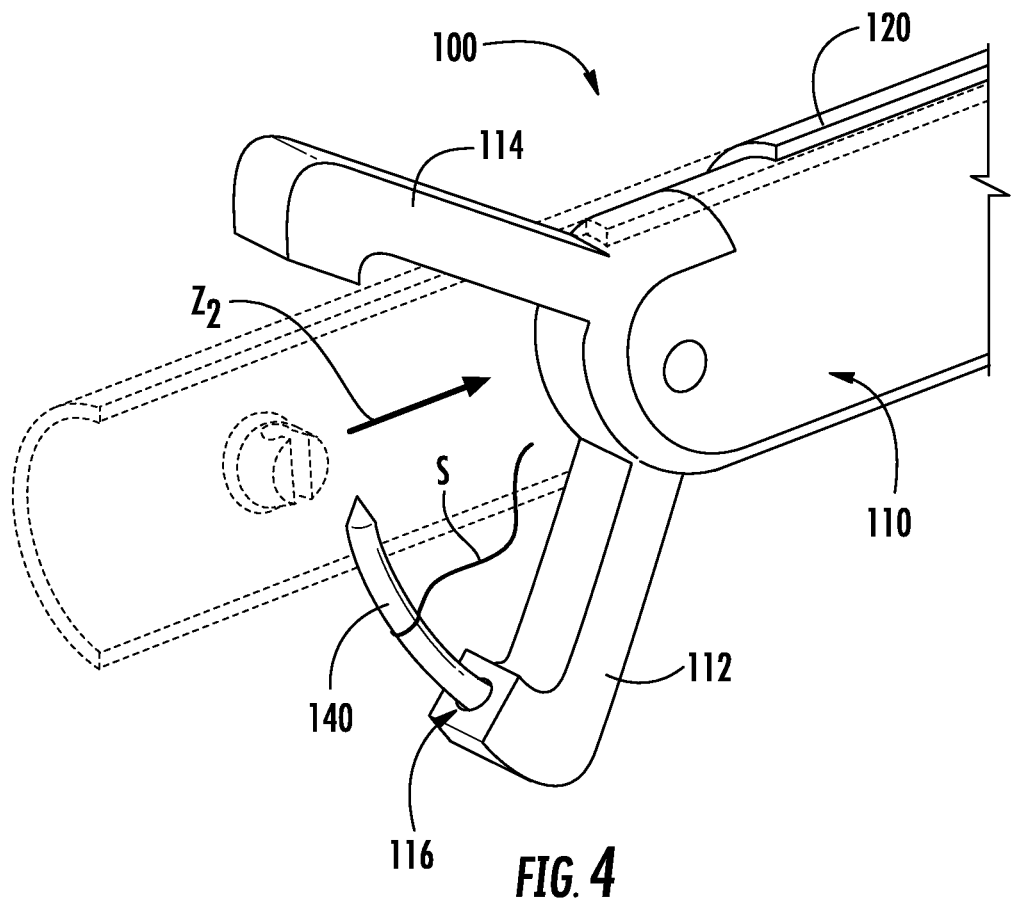
FIG. 4 is a perspective view of the distal end portion of the end effector assembly of FIGS. 2 and 3 illustrating the end effector in the open state, the housing in a second retracted state, and the needle supported on the end effector.

As seen in FIG. 4, upon securing needle 140 to end effector 110 and separating needle 140 from mounting member 130, housing 120 can be slid further proximally, as indicated by arrow "$Z_2$," to a suturing position or a second retracted state so that a distal end of housing 120 is disposed proximally of first and second jaw members 112, 114 to enable first and second jaw members 112, 114 to pivot between open and closed configurations to effectuate a suturing procedure.

Figure 5:
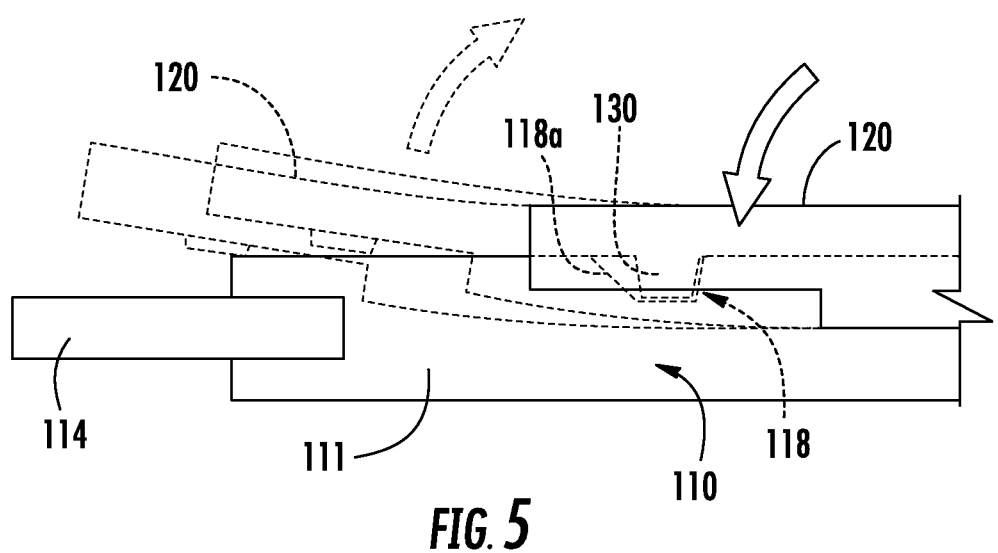
FIG. 5 is a top, elevational view of FIG. 4 illustrating the housing being moved to the second retracted state relative to the end effector.

With reference to FIG. 5, body member 111 defines a recess 118 within which mounting member 130 can be seated to maintain housing 120 secured in the second retracted state. Housing 120 can be adapted to be flexed outwardly and/or inwardly (relative to the longitudinal axis "L") as housing 120 is slid along body member 111 of end effector 110 so that mounting member 130 can snap into and/or out of recess 118 of body member 111 of end effector 110. In certain embodiments, recess 118 can be keyed, for example, with one or more tapered surfaces 118a that enable mounting member 130 to be inserted and/or released to/from recess 118 upon a slight manipulation of housing 120, such as by rotation and/or axial translation of housing 120 relative body member 111. This rotation and/or axial translation causes mounting member 130 to cams into and/or out of recess 118.

After moving housing 120 to the second retracted state, the end effector 110 can then be used to effectuate a suturing procedure as described in U.S. Pat. No. 8,337,515 referenced above. For example, handle assembly 20 is actuated, for example, upon an actuation of trigger 24 of handle assembly 20 (FIG. 1), to pivot one or both of first and second jaw members 112, 114 between open and closed states for passing surgical needle 140 between jaw members 112, 114 and drawing suture "S" through tissue. More particularly, with needle 140 secured to an initial one of jaw members 112, 114, an actuation of trigger 24 of handle assembly 20 closes jaw members 112, 114 around tissue so that needle 140 pierces the tissue and is guided into the needle receiving recess 116 of the other jaw member 112, 114 to secure needle 140 thereto and effectuate a first stitch. Jaw members 112, 114 can then be opened again so that needle 140 can be transferred back to the initial one of jaw members 112, 114 in like fashion upon another closing of jaw members 112, 114 to effectuate another stitch. This process, in whole, or in part, can be repeated as necessary until the tissue is sutured as desired.

Upon completion of the suturing procedure, needle 140 can then be re-secured to housing 120 by reversing the steps. More specifically, the distal end portion of housing 120 is advanced distally past end effector 110 to the first retracted state and jaw members 112, 114 are pivoted to position needle 140 into channel 138 with mounting member 130 oriented, for example, at a perpendicular angle relative the longitudinal axis "L" of mounting member 130 e.g., in the second, deployed position (see FIG. 3). Mounting member 130 can then be rotated, for example, upon an actuation of actuator 22. The rotation of mounting member 130 rotates needle 140 until needle 140 extends lengthwise or longitudinally along longitudinal axis "L," e.g., to the first, insertion position, to establish a minimal profile for extraction of end effector assembly 100 through, for example, a 10 millimeter diameter cannula assembly (not shown) or other small opening. Then, end effector assembly 100 may be removed from the surgical site through cannula assembly or other small opening.

In some embodiments, housing 120 defines a groove along an outer surface of body member 111 of end effector 110. The groove can be aligned with recess 118 of body member 111 and can be adapted to releasably receive mounting member 130, or portions thereof, as mounting member 130 slides along body member 111.

In certain embodiments, body member 111 of end effector 110 can include a linear and/or curvilinear spline adapted to engage channel 138 of mounting member 130 for enabling housing 120 to slid along body member 111 of end effector 110 and/or for selectively locking housing 120 in a fixed state (e.g., curving spline) on body member 111. In embodiments, actuator 22 can be actuated to rotate mounting member 130 to conform to changes in the spline direction.

In some embodiments, mounting member 130 is freely rotatable. In embodiments, one or both of jaw members 112, 114 can be adapted to engage needle 140 upon a pivoting movement of one or both jaw members 12, 114 to an open and/or closed configuration such that the engagement with needle 40 rotates needle 140 (and mounting member 130) without an actuation of actuation mechanism 150.

Any of the components of the presently described devices can be formed of any suitable metallic and/or polymeric material. Securement of any of the components of the presently described devices to any of the other components of the presently described devices can be effectuated using known fastening techniques such welding (e.g., ultrasonic), crimping, gluing, etc.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, when finished using the present minimally invasive suturing devices, removal from the surgical site may be achieved while the needle is in the second, deployed position by first removing the access device (e.g., cannula) and then simply pulling the suturing device through the incision in the patient's skin, which will have sufficient elasticity to enable removal of the suturing device with out reducing the height of the end effector. As another example, the needle may be released from both jaw members and separated from the end effector (e.g., with a separate grasping device) so that the jaw members may be closed and withdrawn through the access device separate from the needle.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An end effector assembly for a surgical stitching device, comprising:
    an end effector including a first jaw member and a second jaw member;
    a housing movable relative to the end effector, the housing including a mounting member; and
    a needle releasably coupled to the housing and movable relative to the housing between a first, insertion position and a second, deployed position, the needle adapted, when in the second, deployed position, to releasably couple to at least one of the first jaw member and the second jaw member of the end effector,
    wherein the mounting member is adapted to releasably couple the needle to the housing and enable the needle to rotate between the first, insertion position and the second, deployed position.

2. The end effector assembly of claim 1, wherein the needle is rotatable relative to the housing.

3. The end effector assembly of claim 1, wherein the end effector defines a longitudinal axis, the housing is axially movable along the longitudinal axis relative to the first and second jaw members.

4. The end effector assembly of claim 1, wherein the first jaw member is pivotable relative to the second jaw member between open and closed configurations.

5. The end effector assembly of claim 1, wherein the mounting member includes a pair of protuberances that defines a channel between the pair of protuberances, the channel adapted to receive the needle.

6. The end effector assembly of claim 1, wherein the housing is C-shaped.

7. An end effector assembly, comprising:
    an end effector including a first jaw member and a second jaw member and defining a longitudinal axis;
    a housing operably coupled to the first and second jaw members of the end effector, the housing including a mounting member, the housing being axially movable relative to the first and second jaw members of the end effector;
    a needle supported on the housing and defining a centerline that extends through opposed ends of the needle, the needle being rotatable relative to the housing between a first position and at least a second position, the needle adapted to rotate about an axis of rotation that extends through the housing transverse to the longitudinal axis of the end effector, the centerline of the needle being longitudinally aligned with the longitudinal axis of the end effector in the first position and being angled relative to the longitudinal axis of the end effector in the second position, wherein the mounting member is adapted to releasably secure the needle to the housing and enable the needle to rotate relative to the housing.

8. The end effector assembly of claim 7, wherein the first jaw members is pivotable relative to the second jaw member between open and closed configurations.

9. The end effector assembly of claim 7, wherein the mounting member includes a pair of protuberances that defines a channel that extends between the pair of protuberances, the channel adapted to receive the needle.

10. The end effector assembly of claim 7, wherein the housing is C-shaped.

11. A surgical stitching device, comprising:
a handle;
an elongate member extending from the handle;
an end effector assembly supported on the elongate member, the end effector assembly including:
an end effector defining a longitudinal axis and including a first jaw member, a second jaw member, and a body member, the first and second jaw members pivotably coupled to the body member, the body member defining a recess;
a housing operably coupled to the first and second jaw members of the end effector, the housing including a mounting member and being axially movable relative to the first and second jaw members of the end effector between an extended state and a retracted state, the mounting member being receivable within the recess of the body member of the end effector to releasably retain the housing in the retracted state;
a needle releasably supported on the housing by the mounting member, the needle adapted to selectively couple to at least one of the first and second jaw members.

12. The surgical stitching device of claim 11, wherein the needle defines a centerline that extends through opposed ends of the needle, the needle being selectively supported on the housing and adapted to rotate about an axis of rotation that extends through the housing transverse to the longitudinal axis of the end effector, the needle being rotatable between a first position and at least a second position when supported on the housing, the centerline of the needle being longitudinally aligned with the longitudinal axis of the end effector in the first position and being angled relative to the longitudinal axis of the end effector in the second position.

13. The surgical stitching device of claim 11, wherein the mounting member includes a pair of protuberances that defines a channel between the pair of protuberances, the channel adapted to receive the needle.

14. The surgical stitching device of claim 11, wherein the first jaw member is pivotable relative to the second jaw member between open and closed configurations.

15. The surgical stitching device of claim 11, wherein the end effector is movable between open and closed states, the end effector defining a height measured between a bottom most surface of the end effector and a top-most surface of the end effector, the needle defining a working length that is greater than the height of the end effector.

* * * * *